(12) United States Patent  
Compton et al.

(10) Patent No.: US 8,016,998 B2  
(45) Date of Patent: Sep. 13, 2011

(54) ELECTROCHEMICAL DETECTION OF ARSENIC

(75) Inventors: Richard Guy Compton, Oxford (GB); Xuan Dai, Oxford (GB)

(73) Assignee: Isis Innovation Limited, Summertown, Oxford (GB)

(*) Notice: Subject to any disclaimer, the term of this patent is extended or adjusted under 35 U.S.C. 154(b) by 588 days.

(21) Appl. No.: 12/090,978

(22) PCT Filed: Oct. 23, 2006

(86) PCT No.: PCT/GB2006/003957  
§ 371 (c)(1), (2), (4) Date: Jun. 18, 2008

(87) PCT Pub. No.: WO2007/045916  
PCT Pub. Date: Apr. 26, 2007

(65) Prior Publication Data  
US 2008/0245670 A1 Oct. 9, 2008

(30) Foreign Application Priority Data

Oct. 21, 2005 (GB) .................................. 0521440.8  
Nov. 26, 2005 (GB) .................................. 0524152.6

(51) Int. Cl.  
*G01N 27/333* (2006.01)  
(52) U.S. Cl. ..................................... 205/789.5; 204/416  
(58) Field of Classification Search ................ 205/789, 205/789.5, 775; 204/416–418  
See application file for complete search history.

(56) References Cited

U.S. PATENT DOCUMENTS 4,842,698 A 6/1989 Kirchnerova et al.  
2005/0067279 A1 3/2005 Chen

FOREIGN PATENT DOCUMENTS

RU 2105297 2/1998  
WO 9964366 12/1999  
WO 0001635 1/2000

OTHER PUBLICATIONS

Wei et al., "Cyclic voltammetric study of arsenic reduction and oxidation in hydrochloric acid using a Pt RDE," Journal of Applied Electrochemistry 34, 241-244, 2004.*

Shen et al., "Preparation of Multilayer Films Containing Pt Nanaoparticles on a Glassy Carbon Electrode and Application as an Electrocatalyst for Dioxygen Reduction," Langmuir 2003, 19, 5397-5401.*

Mo et al., "Electrochemical characterization of unsupported high area platinum dispersed on the surface of a glassy carbon rotating disk electrode in the absence of Nafion® or other additives," Journal of Electroanalytical Chemistry 538-539 (2002) 35-38.*

(Continued)

*Primary Examiner* — Alex Noguerola  
(74) *Attorney, Agent, or Firm* — Kirton & McConkie; Evan R. Witt

(57) ABSTRACT

Electrochemical methods and materials for the detection of arsenic. In one aspect, arsenic is detected using a working electrode comprising particulate platinum. In another aspect, arsenic is detected using an electrode comprising indium tin oxide and particulate gold. Also provided are methods for the production of electrodes which involve the electrodeposition of gold onto indium tin oxide.

13 Claims, 6 Drawing Sheets

OTHER PUBLICATIONS

Forsberg et al.. "Determination of Arsenic by Anodic Stripping Voltammetry and Differential Pulse Anodic Stripping Voltammetry," Analytical Chemistry, vol. 47, No. 9, Aug. 1975.*

Zhang, J et al "Seed Mediated Growth of Gold Nanoparticles on Indium Tin Oxide Electrodes: Electrochemical Characterization and Evaluation".

Xuan, D et al "Direct Electrodeposition of Gold Nanoparticles onto Indium Tin Oxide Film Coated Glass: Application to the Detection of Arsenic(III)".

Simm, A et al "Novel Methods for the Production of Silver Microelectrode-Arrays: Their Characterization by Atomic Force Microscopy and Application to the Electro-reduction of Halothane".

Dai Xuan et al.: "Anodic stripping voltammetry of arsenic(III) using gold nanoparticle-modified electrodes." Analytical Chemistry. Oct. 1, 2004, vol. 76, No. 19, pp. 5924-5929, XP002413694.

Martel D et al.: "The effect of modification of carbon electrodes with hybrid inorganic/organic monolayers on morphology and electrocatalytic activity of platinum deposits" Electrochimica Acta, Elsevier Science Publishers, Barking, GB, vol. 46, No. 26-27, Aug. 24, 2001, pp. 4197-4204, XP004309886.

Dai Xuan et al.: "Gold nanoparticle modified electrodes show a reduced interference by Cu(II) in the detection of As (III) using anodic stripping voltammetry" Electroanalysis, vol. 17, No. 14, Jul. 2005, pp. 1325-1330, XP002413695.

Wang S et al.: "Electrodeposition of Pt-Fe(III) nanoparticle on glassy carbon electrode for electrochemical nitric oxide sensor" Electrochimica Acta, Elsevier Science Publichers, Barking, GB, vol. 50, No. 14, May 5, 2005, pp. 2887-2891, XP004857526.

Cui H-F et al.: "Electrocatalytic reduction of oxygen by a platinum nanoparticle/carbon nanotube composite electrode" Journal of Electroanalytical Chemistry and Interfacial Electrochemistry, Elsevier, Amsterdam, NL, vol. 577, No. 2, Apr. 1, 2005, pp. 295-302, XP004786536.

Tang H et al.: "Amperometric glucose biosensor based on adsorption of glucose oxidase at platinum nanoparticle-modified carbon nanotube electrode" Analytical Biochemistry, Academic Press, New York, NY, vol. 331, No. 1, Aug. 1, 2004, pp. 89-97, XP004520199.

Hung D Q et al.: "Analytical methods for inorganic arsenic in water: a review" Talanta, Elsevier, Amsterdam, vol. 64, No. 2, Oct. 8, 2004, pp. 269-277, XP004544865.

Welch Christine M et al.: "The use of nanparticles in electroanalysis: A review" Anal. Bioanal. Chem.; Analytical and Bioanalytical Chemistry, Feb. 2006, vol. 384, No. 3, pp. 601-619, XP002413696.

Zhang J et al.: "Gold nanoparticle-attached ITO as a biocompatible matrix for myoglobin immobiliation: direct electrochemistry and catalysis to hydrogen peroxide" Journal of Electroanalytical Chemistry and Interfacial Electrochemistry, Elsevier, vol. 577, No. 2, Apr. 1, 2005, pp. 273-279, XP004786533.

Zhang J et al.: "Gold nanoparticle arrays directly grown on nanostructured indium tin oxide electrodes: Characterization and electroanalytical application" Analytica Chimica Acta, Elsevier, vol. 540, No. 2, Jun. 1, 2005, pp. 299-306, XP004889841.

Zhang Jingdong et al.: "A novel electrode surface fabricated by directly attaching gold nanospheres and nanorods onto indium tin oxide substrate with a seed mediated growth process" Electrochem. Commun.; Electrochemistry Communications Jul. 7, 2004, pp. 683-688, XP002428701.

Jaramillo T F et al.: Catalytic activity of supported Au nanoparticles deposited from block copolymer micelles' Journal of the American Chemical Society United States, Jun. 18, 2003, vol. 125, No. 24, pp. 7148-7149, XP002428702.

Feeney R et al.: "On-site analysis of arsenic in groundwater using a microfabricated gold ultramicroelectrode array" Analytical Chemistry United States, May 15, 2000, vol. 72, No. 10, pp. 2222-2228, XP002428703.

Simm Andrew O et al.: "A comparison of different types of gold-carbon composite electrode for detection of arsenic (III)." Analytical and Bioanalytical Chemistry, vol. 381, No. 4, Feb. 2005, pp. 979-985, XP002428704.

Bharathi S et al.: "A glucose biosensor based on electrodeposited biocomposites of gold nanoparticles and glucose oxidase enzyme." The Analyst, vol. 126, No. 11, Nov. 2001, pp. 1919-1922, XP002428705.

* cited by examiner

ELECTROCHEMICAL DETECTION OF ARSENIC

FIELD OF THE INVENTION

This invention relates to electrochemical detection, in particular the detection of arsenic. The invention also relates to electrode materials suitable for use in the detection of arsenic, and to methods for their production.

BACKGROUND TO THE INVENTION

Arsenic is a naturally occurring element that is widely distributed in the earth's crust. Exposure to arsenic can cause a variety of adverse health effects, including dermal changes, respiratory, cardiovascular, gastrointestinal, genotoxic, mutagenic and carcinogenic effects. Arsenic contamination of drinking water has been widely reported in Argentina, Bangladesh, Cambodia, Chile, China, Ghana, Hungary, Inner Mongolia, Mexico, Nepal, New Zealand, Philippines, Taiwan, the United States and Vietnam.

The World Health Organization's arsenic guideline value for drinking water is 10 ppb. Many detection methods have been developed to detect such levels of arsenic. The most reliable techniques are more suitable for laboratory conditions only and are generally time consuming. In contrast, electrochemical methods provide accurate measurements of low concentrations of metal ions at the ppb levels with rapid analysis times and low cost instrumentation. Arsenic can be detected using electrochemical stripping voltammetry methods. Forsberg et al [(1975) Anal Chem 47:1586] describe the determination of arsenic by anodic stripping voltammetry (ASV) and differential pulse anodic stripping voltammetry (DPSAV) at various electrode materials (Hg, Pt and Au). Simm et al [(2004) Anal Chem 76:5051] disclose the sonoelectroanalytical arsenic detection on a gold electrode. Most recently, using anodic stripping voltammetry at a gold nanoparticle modified glassy carbon (GC) electrode, a limit of detection (LOD) of 0.0096 ppb was obtained [Dai et al., (2004) Anal Chem 76:5924].

Although gold and platinum electrodes can be used to determine As (III) levels via anodic stripping voltammetry, the use of such electrodes is hindered by the interference of other metals, for example lead, copper, zinc, iron, antimony, silver, selenium, bismuth and mercury. Among these metals, copper (in the form of Cu (II)) is by far the most common and ubiquitous in water systems; indeed copper is found in relatively high levels in the world's water supplies. Thus, Cu (II) potentially presents a serious interference problem in arsenic detection, especially if conventional stripping voltammetry is employed. At a gold macroelectrode, Cu codeposits with As during the pre-deposition step and forms the intermetallic compound $Cu_3As_2$ as well as bulk copper metal. The stripping peak of Cu is seen at a similar but slightly more positive potential than the As stripping peak. If the concentration of Cu (II) is sufficiently high then the stripping peak of Cu (II) partly masks the As (III) signal. A separate stripping peak, which is close to the arsenic stripping peak, due to $Cu_3As_2$ is also observable so that three maxima are possible in the stripping curve of arsenic when Cu (II) is present (see FIG. 1 herein).

The oxidation of As (III) to As (V) can be detected using a platinum electrode. Lown et al [(1980) Anal Chim Acta 116:41] have detected arsenic (III) by oxidation at a platinum wire electrode in perchloric acid solution using a flow-through cell. Williams et al [(1992) Anal Chem 64:1785] performed pulsed voltammetric detection of arsenic (III) using a rotating disk platinum electrode. In both these cases, significant levels of arsenic were employed.

There remains a need for an electrochemical method of detecting arsenic which is unperturbed by the interference of other metals, in particular copper. There also remains a need for electrode materials which have a desirable limit of detection (LOD) for arsenic, and which can be fabricated readily and at low cost.

Cui et al [(2005), J Electroanal Chem, 577:295] describe a carbon electrode modified with nanoparticulate platinum. This electrode is described as being useful in the electrocatalytic reduction of oxygen.

Indium tin oxide (ITO) films are of great interest because of their high optical transparency and good electrical conductivity. Gold nanoparticle-modified ITO glass electrodes have been used in the electrochemical detection of nitric oxide, oxygen, hydrogen peroxide and carbon monoxide. Gold nanoparticles have been grown onto ITO coated glass by seed-mediated growth (Zhang et al, Anal. Chim. Acta., 2005, 540, 299; Zhang et al, Electrochem. Commu., 2004, 6, 683; and Zhang et al., Electroanal. Chem., 2005, 577, 273) or by assembling with polymer (Huang et at, Anal. Chim. Acta., 2005, 535, 15; Patolsky et al, J. Electroanal. Chem., 1999, 479, 69; and Jaramillo et al, J. Am. Chem. Soc., 2003, 125, 7148.26-28).

SUMMARY OF THE INVENTION

The present invention is based in part on a discovery that interference of the type described above can be avoided by using an electrode modified with platinum particles, in particular platinum nanoparticles. Furthermore, the use of such an electrode may result in an improved sensitivity compared with other (e.g. platinum-based) electrodes.

Accordingly, in a first aspect the present invention provides a method of detecting arsenic in a sample, which comprises the steps of contacting the sample with working and counter electrodes in the presence of an electrolyte, and determining the electrochemical response of the working electrode to the sample, wherein the working electrode comprises particulate platinum.

A second aspect of the invention is the use of an electrode comprising particulate platinum, for the detection of arsenic.

The present invention is also based in part on a discovery that ITO electrodes comprising particulate gold can be used to detect arsenic at low concentrations. It has also been found that ITO electrodes can be made by electrodepositing gold on an ITO glass substrate, providing a simple, low-cost alternative to conventional manufacturing techniques.

Accordingly, in a further aspect the present invention provides a method of detecting arsenic in a sample, which comprises the steps of contacting the sample with working and counter electrodes in the presence of an electrolyte, and determining the electrochemical response of the working electrode to the sample, wherein the working electrode comprises indium tin oxide and particulate gold.

Another aspect of the invention is the use of an electrode for the detection of arsenic, wherein the electrode comprises indium tin oxide and particulate gold.

Another aspect of the invention is a method of producing an electrode material which comprises contacting a substrate with an electrolyte comprising gold ions and applying a potential across the substrate and a counter electrode such that gold is deposited on the substrate, wherein the substrate comprises indium tin oxide.

Using a method of manufacture of the invention, electrodes may be readily fabricated at low cost and have greater stability than conventional electrodes. Thus, the electrodes are particularly suited for use as disposable electrodes for in field analysis.

DESCRIPTION OF VARIOUS EMBODIMENTS

Figure 1:
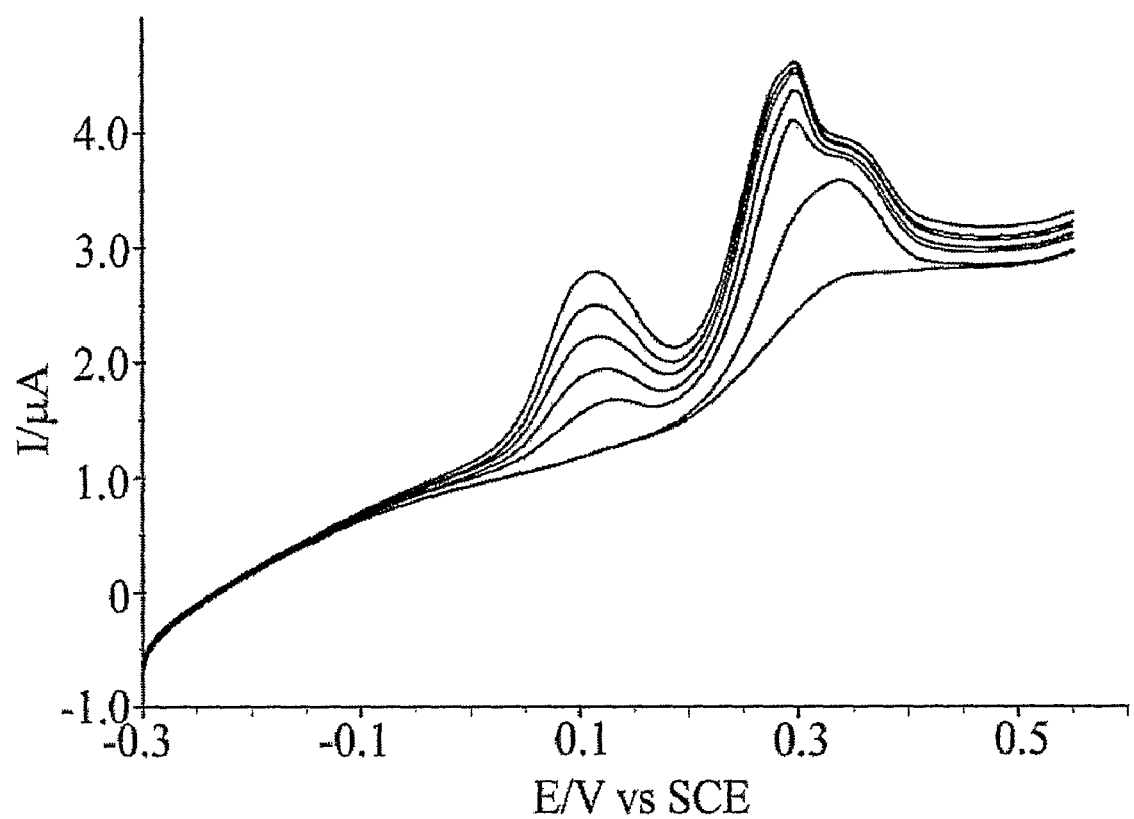
FIG. 1 shows linear sweep voltammetry (LSV) curves for As (III) additions (1 µM each) to 10 µM Cu (II) in 0.1 M $H_2SO_4$ using a gold macro disk electrode (0.008 $cm^2$). LSV parameters: deposition at −0.3 V for 60 sec.

Arsenic present in a sample may be detected by determining the levels of As (III) at a working electrode comprising particulate platinum, especially nanoparticulate platinum. Alternatively, the presence of arsenic in a sample may be detected by determining the levels of As (III) at a working electrode comprising ITO and particulate gold.

The sample is typically a liquid sample, e.g. an aqueous sample such as drinking water. The sample may contain one or more other metals, for example, selected from copper, lead, zinc, iron, antimony, silver, selenium, bismuth and mercury. In one embodiment of the invention, the sample comprises copper (e.g. in the form of Cu (II)).

In one aspect, the working electrode comprises particulate platinum, more preferably nanoparticulate platinum. The terms "nanoparticulate" and "nanoparticle" as used herein refer to one to more particles having a diameter of the order of nanometers (nm). The or each particle may have a diameter of from about 10 to about 900 nm, more preferably from about 10 to about 500 nm. More particularly, the or each particle may have E diameter of from about 25 to about 200 nm, e.g. from about 50 to about 175 nm. The average diameter of the one or more particles is preferably from about 100 to about 200 nm, more preferably from about 100 to 185 nm. The particle density at the electrode may vary from about 0.1 to about 100 particles/$µm^2$, e.g. from about 0.5 to about 50 particles/$µm^2$. In particular, the particle density may vary from about 0.1 to about 10 particles/$µm^2$, more particularly from about 0.5 to about 9.0 particles/$µm^2$. The electrode may comprise a substrate and, supported thereon, platinum particles. For example, the platinum particles may be supported on glassy carbon.

In another aspect, the working electrode comprises particulate gold, more preferably nanoparticulate gold. The or each particle preferably has a diameter of from about 10 to about 900 nm, more preferably from about 10 to about 500 nm, more preferably from about 25 to about 200 nm. The particle density at the electrode may vary from about 0.1 to about 100 particles/$µm^2$, more preferably from about 0.5 to about 50 particles/$µm^2$, more preferably from about 0.5 to about 10 particles/$µm^2$. The working electrode typically comprises ITO and, supported thereon, particulate gold.

Particle size and density may be confirmed using atomic force microscopy (AFM). The size of the particles may be selected to obtain optimum sensitivity.

Working electrodes of the invention may be prepared according to any suitable procedure known in the art, e.g. chemical synthesis, UV light irradiation or electron beam irradiation.

With regard to platinum-based electrodes, of particular mention are the procedures of Cui et al (see above), which describes the production of a platinum nanoparticle/carbon nanotube composite electrode. Preferably, the working electrode is obtained by the deposition of $PtCl_6^{2-}$ at a standard working electrode, preferably a glassy carbon (GC) electrode. The $PtCl_6^{2-}$ species can be applied by potential cycling, and the size and density of the resulting nanoparticulate platinum varied by controlling the number of potential cycles. By way of example, 1 to 50 cycles may be applied, a preferred number being about 25 cycles.

With regard to ITO-gold electrodes, a particularly preferred method of manufacture is electrochemical deposition of gold on an ITO. Preferably, the working electrode is obtained by the electrodeposition of $AuCl_4^-$ on indium tin oxide glass. The concentration of the gold (e.g. $AuCl_4^-$) species is typically from about 0.01 to about 1.0 mM, in particular 0.1 mM. The electrolyte is typically in solution and may comprise an acid, such as sulphuric acid. The size and density of the gold particles can be controlled by varying the time of application and/or magnitude of the potential. For example, the potential may be applied for about 25 to about 300 s, and may be varied from about +1.055 to about −0.045 V (vs. a saturated calomel electrode).

The electrochemical response of the working electrode may be determined using any suitable technique known in the art. This typically involves applying a potential across the working and counter electrodes, and determining the response of the working electrode to the sample. A potential may be applied across the electrodes using a potentiostat, and the response of the cell to the sample determined.

Detection may take place using any suitable electrolyte known in the art. The electrolyte is generally present in solution. In particular, the electrolyte may comprise an acidic species, for example, $HClO_4$, $H_2SO_4$, $HNO_3$ or $H_3PO_4$, in aqueous solution. Preferably, the electrolyte is an aqueous solution of $HClO_4$ or HCl. The concentration of the electrolyte solution is typically from about 0.1 to about 1.5 M, more preferably from about 0.1 to about 1 M (particularly when the electrolyte is acidic). The counter electrode can be any suitable electrode known in the art. In one embodiment, a platinum counter electrode (e.g. platinum wire) is used. The potential may be applied relative to a reference electrode, e.g. a saturated calomel electrode (SCE). The application of potential and the determination of the response may be achieved using a potentiostat. Linear sweep or cyclic voltammetric techniques may be utilised in the present invention. Direct anodic scan voltammetry may also be used. Particularly when linear sweep voltammetry is used, detection preferably takes place in the presence of nitric acid, in order to minimise the effects of oxygen deposition. Thus, for example, nitric acid may be present in an electrolyte solution.

The following Examples illustrates the invention.

EXPERIMENTAL

Reagents and Chemicals: Example 1

Potassium hexachloroplatinate (IV) ($K_2PtCl_6$, 98%) and potassium chloride (KCl, 99.5%) were obtained from Sigma-Aldrich. Cupric sulphate ($Cu_2SO_4.5H_2O$, 99.5%) and sulfuric acid ($H_2SO_4$, 98%) were from BDH. Sodium (meta) arsenite ($NaAsO_2$, 99%) was purchased from Fluka. All the reagents were used without further purification. All solutions and subsequent dilutions were prepared using purified water from Vivendi UHQ grade water system with a resistivity of not less than 18 MD cm. As (III) stock solution (10 mM) was prepared from $NaAsO_2$: 0.013 g $NaAsO_2$ was dissolved in 10 mL purified water. Cu (II) stock solution (10 mM) was made by dissolving 0.0624 g cupric sulphate ($Cu_2SO_4.5H_2O$, BDH) in 25 mL purified water.

Reagents and Chemicals: Examples 2 and 3

All the reagents were of analytical grade and were used without further purification. Hydrogen tetrachloroaurate (III) trihydrate ($HAuCl_4.3H_2O$, 99.9+%) was obtained from Sigma-Aldrich. Sodium (meta) arsenite ($NaAsO_2$, 99%) was purchased from Fluka. All solutions and subsequent dilutions were prepared using deionised water from Vivendi UHQ grade water system with a resistivity of not less than 18 MΩ cm. As (III) stock solution (10 mM) was prepared by dissolving 0.013 g $NaAsO_2$ in 10 mL deionised water.

ITO film coated glass (Sigma-Aldrich) having a working area of 1×1 $cm^2$ and a resistance of 70-100 ohm was used to construct the working electrode.

Instrumentation: Example 1

Electrochemical measurements were recorded using an Autolab PGSTAT 30 computer controlled potentiostat (Eco-Chemie) with a standard 3-electrode system. Platinum nanoparticle modified glassy carbon electrodes (GCE, geometric area of 0.07 $cm^2$, BAS technical) and platinum macroelectrodes (geometric area of 0.07 $cm^2$) served as working electrodes, and a platinum wire was used as a counter electrode with a saturated calomel reference electrode (SCE, Radiometer). Between each modification, the GC electrode was polished with alumina powder (Micropolish II, Buehler) using decreasing particle sizes from 1 μm to 0.3 μm. The electrode was sonicated for 10 min in deionized water after each stage of polishing. All experiments were carried at a temperature 20±2° C.

The AFM measurements were performed using a Digital Instruments Multimode SPM, operating in ex situ contact mode. A model 'J' scanner was used having a lateral range of 125×125 μm and a vertical range of 5 μm. Standard silicon nitride probes (type NP, Digital Instruments Multimode SPM), having a force constant of approximately 0.58 $Nm^{-1}$ were used.

Instrumentation: Examples 2 and 3

Electrochemical measurements were recorded using an Autolab PGSTAT 30 computer controlled potentiostat (Eco-Chemie) with a standard three-electrode system. A platinum wire was used as a counter electrode, and a saturated calomel reference electrode (Radiometer) completed the cell assembly. All experiments were carried at a temperature of 20±2° C.

AFM measurements were performed using a Digital Instruments Multimode SPM, operating in ex situ tapping mode. A model 'J' scanner was used having a lateral range of 125×125 μm and a vertical range of 5 μm. Standard silicon nitride probes (type NP, Digital Instruments Multimode SPM), having a force constant of approximately 0.58 $Nm^{-1}$ were used.

EXAMPLE 1

Detection of Arsenic Using Platinum Nanoparticle-Modified Electrodes

The electrochemical detection of As (III) at a platinum nanoparticle modified glassy carbon electrode in 1 M aqueous $HClO^4$ was investigated. Platinum nanoparticle-modified glassy carbon electrodes were prepared by potential cycling in 0.1 M aqueous KCl containing 1 mM $K_2PtCl_6$. In each cycle, the potential was held at +0.5 V for 0.01 seconds and at −0.7 V for 10 s. The resulting electrode surfaces were characterized by atomic force microscopy (ARM). The response to As (III) at the modified electrode was examined using cyclic voltammetry and linear sweep voltammetry.

Preparation of Platinum Nanoparticle-Modified Electrodes

The procedure for the deposition of platinum nanoparticles at GC was adapted from the teachings of Cui et al., (2005) J Electroanal Chem 577:295. The polished GC electrode was immersed into solutions of 1 mM $PtCl_6^{2-}$ in 0.1 M KCl, and subjected to potential cycling for 1, 5, 10, 25 or 50 cycles. In each cycle, the potential was stepped to +0.5 V for 0.01 seconds then to −0.7 V for 10 seconds. Comparison experiments were also made by applying 1 potential cycle stepped to +0.5 V for 0.01 seconds then to −0.7 V for 120 seconds. The effect of applying the positive potential +0.5 V for 0.01 seconds was also examined. All solutions were de-gassed with a nitrogen stream prior to each measurement for at least 10 minutes.

Characterization of Platinum Nanoparticle Deposition

The surfaces of different platinum nanoparticle-modified glassy carbon electrodes were scanned. In each case, the deposit was made from a $PtCl_6^{2-}$ solution at a concentration of 1 mM. On a clean GC electrode surface, no deposits were observed. Clear small particles could be seen after just one potential cycle (ten seconds deposition). On applying 25 potential cycles, more small isolated particles appear. When 50 potential cycles were used, some particles coagulated. It was also observed that an increase of the number of the potential step cycles (longer total deposition time) resulted in an increase in the density of the platinum particles on the electrode surface. To maximise the number density of platinum particles on the electrode surface without coalescence or film formation, 25 potential cycles were used to prepare the electrodes in the following experiments, except where otherwise stated.

Cyclic Voltammetry of as (III) on Platinum Nanoparticle-Modified Electrodes

Figure 2A:
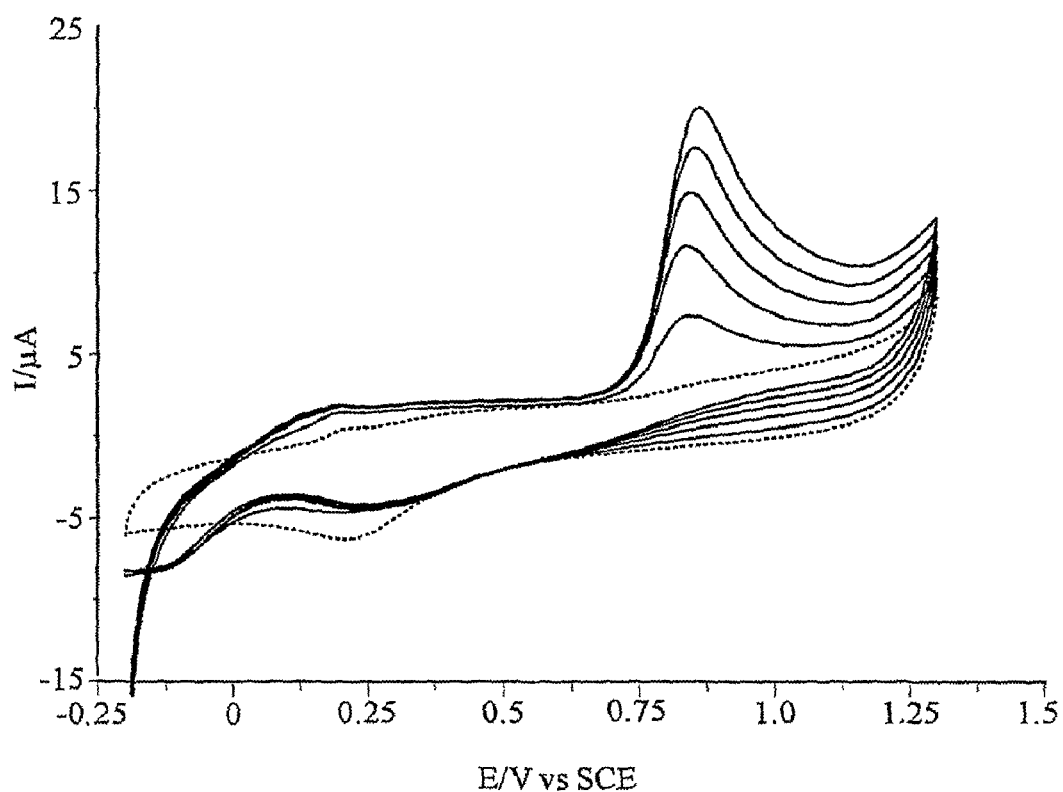
FIG. 2a shows the cyclovoltammetric response of As (III) (100 µM addition each) on platinum nanoparticles electrodeposited on a GC electrode. The electrode was prepared from 0.1 M KCl solution containing 1 mM $PtCl_6^{2-}$ via 25 potential cycles holding at +0.5 V for 0.01 s and at −0.7 V vs SCE for 10 s. The potential scan rate was 100 $mVs^{-1}$.

FIG. 2a shows the typical cyclic voltammetric responses of arsenic (III) additions to 0.1 M $H_2SO_4$ in the range from −0.2 V to +1.3 V (vs SCE, 100 mV s$^{-1}$) of a platinum nanoparticle-modified electrode prepared by applying 25 potential cycles stepped to +0.5 V for 0.01 seconds then to −0.7 V for 10 seconds from 0.1 M KCl containing 1 mM $PtCl_6^{2-}$. The dashed curve is for the solution without arsenic; in the anodic scan, no peak is observed whereas in the cathodic scan, one peak appeared at ca +0.25 V (vs SCE) which can be attributed to the reduction of surface oxide of platinum. With the addition of As (III), the wave more negative than −0.1 V corresponds to the deposition of As (0) and the small wide peak at ca +0.2 V (vs SCE) in the anodic scan is attributed to the oxidation of As (0) to As (III). Another peak was observed at ca +0.85 V (vs SCE) in the anodic scan while the reduction peak of the surface oxide disappeared in the cathodic scan. This peak corresponds to the oxidation of As (III) to As (V).

Figure 2B:
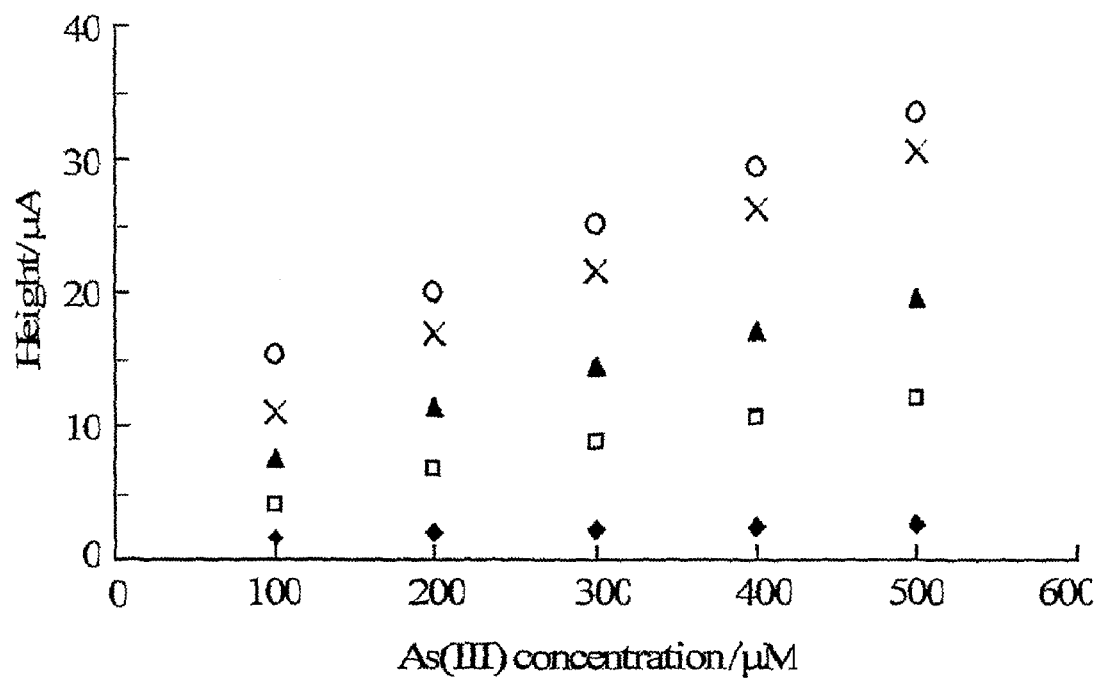
FIG. 2b shows plots of peak heights vs As (III) concentrations at platinum nanoparticle-modified GC electrodes. The electrodes were from prepared 0.1 M KCl solution containing 1 mM $PtCl_6^{2-}$ via various potential cycles holding at +0.5 V for 0.01 s and at −0.7 V vs SCE for 10 s. The legend is as follows: (○) 50 cycles, (X) 25 cycles, (▲) 10 cycles, ((□)) 5 cycles, (□) 1 cycle.
Figure 2C:
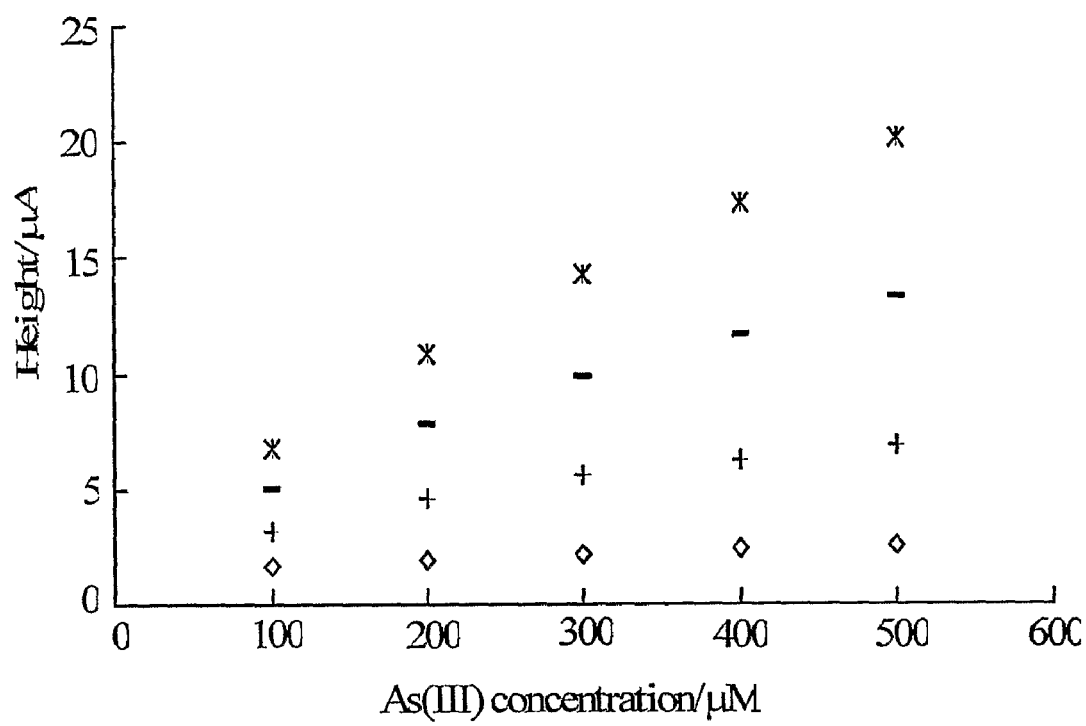
FIG. 2c shows plots of peak heights vs As (III) concentrations at platinum nanoparticle-modified GC electrodes. The electrodes were prepared from 0.1 M KCl solution containing 1 mM $PtCl_6^{2-}$ via 1 potential cycle holding at +0.5 V for 0.01 s and at −0.7 V for various time. The legend is as follows: (+) 120 s, (−) 60 s, (*) 30 s, (□) 10 s.

The peak height increased linearly with the addition of As (III) (from 100 μM to 500 μM). The resulting plots of peak heights vs the concentrations of As (III) are shown in FIG. 2b and FIG. 2c. The comparison of the effect of making the electrodes using different number of potential cycles is shown in FIG. 2b. FIG. 2c shows the effect of the deposition time. Both the increase of the potential cycle number and prolonging the deposition time can increase the sensitivity of As (III) at the resulting electrode.

Comparison with Platinum Macroelectrode

Figure 2D:
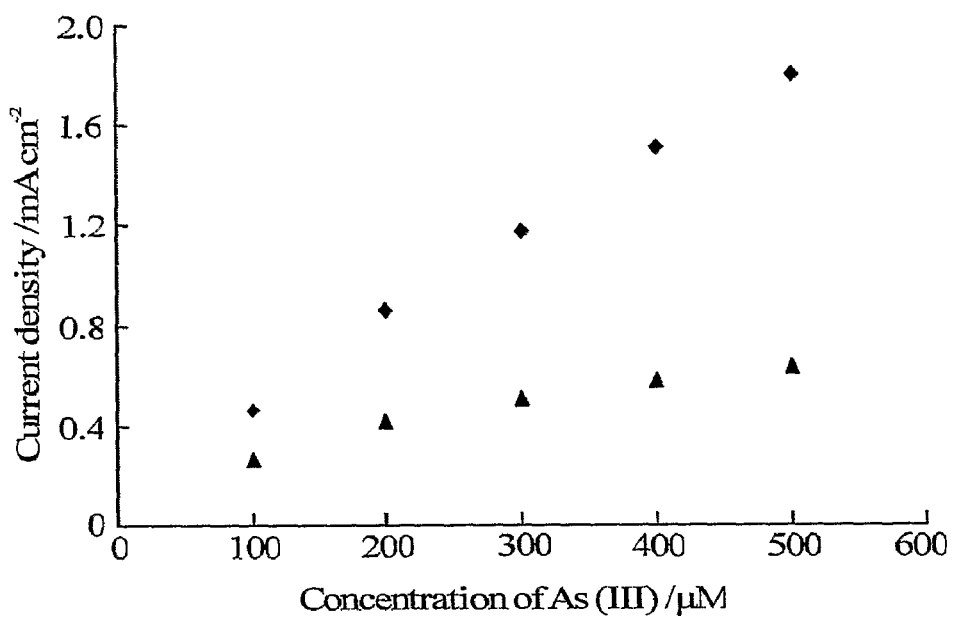
FIG. 2d shows plots of current densities vs As (III) concentrations at (□) the electrode described in the context of FIG. 2a and (▲) a platinum macroelectrode.

A platinum macroelectrode was also employed to perform the CV experiments of As (III) additions to 0.1 M $H_2SO_4$. In order to the compare the results from the platinum macroelectrode and the platinum nanoparticle-modified electrodes, current densities were used for the comparison. For the platinum nanoparticle-modified electrodes (25 potential cycles), the current densities were calculated based on the total surface area of the platinum particles deposited on the GC electrode, which was calculated using the area of the reduction peak of the surface oxide in blank $H_2SO_4$. The area of the platinum macroelectrode was 0.07 cm$^2$. The plots of the current densities vs the concentrations of As (III) are shown in FIG. 2d. The current densities were higher on the platinum nanoparticle-modified GC electrode than on the platinum macro electrode. The platinum nanoparticle-modified GC electrodes resulted in a better sensitivity compared with the platinum macroelectrode.

Interference of Copper (II)

The interference of copper (II) with the detection of arsenic (III) was studied using cyclic voltammetry. Five additions of Cu (II) (100 μM each) were added to 500 μM As (III) in 0.1 M $H_2SO_4$.

Figure 3:
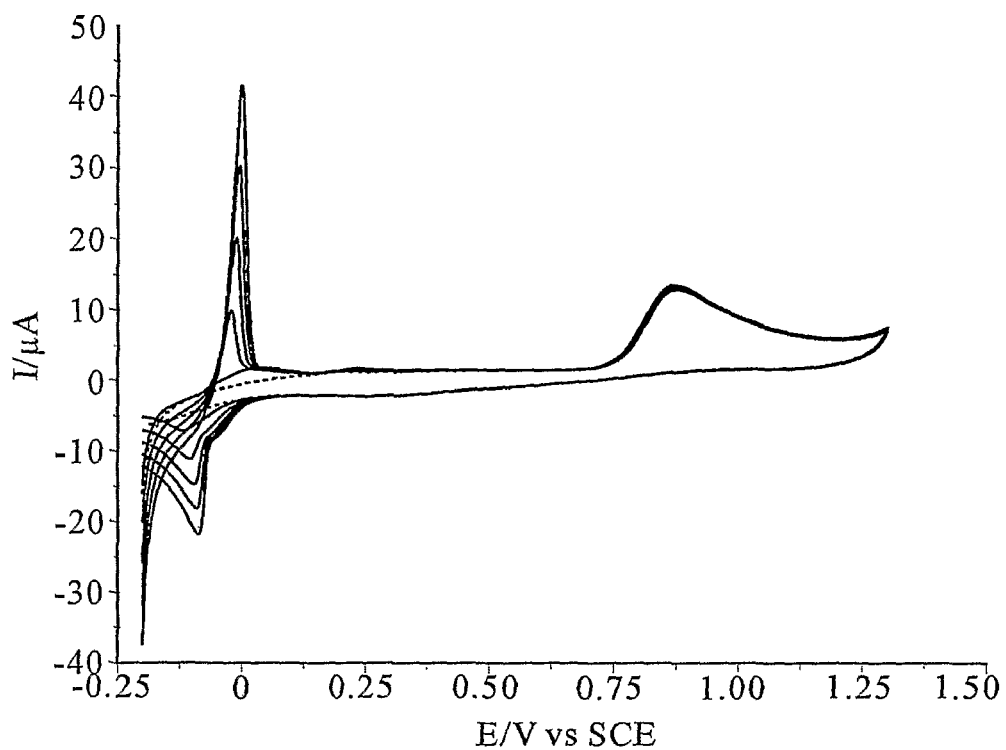
FIG. 3 shows cyclovoltammetric curves for Cu (II) additions (100 µM each) to 100 µm As (III) in 0.1 M $H_2SO_4$ using the electrode described in the context of FIG. 2a. The potential scan rate was 100 $mVs^{-1}$.

In FIG. 3, the dashed curve shows the response for a solution devoid of Cu (II). In the examined potential range from −0.2 V to +1.3 V, there was only one peak near +0.85 V (vs SCE) in the anodic scan which was the oxidation of As (III). With additions of Cu (II), a pair of redox peaks was also found. The oxidation peak was at ca. 0 V (vs SCE and the reduction peak at ca. −0.10 V (vs SCE). The peak height of both the oxidatior peak and the reduction peak increased with the addition of Cu (II). This pair of peaks was far away from the oxidation peak of As (III). The oxidation peak of As (III) was unchanged irrespective of how much Cu (II) (from 100 μM to 500 μM) was added to the solution. It is, therefore, evident that Cu (II) does not interfere with the oxidation peak of As (III).

Figure 4:
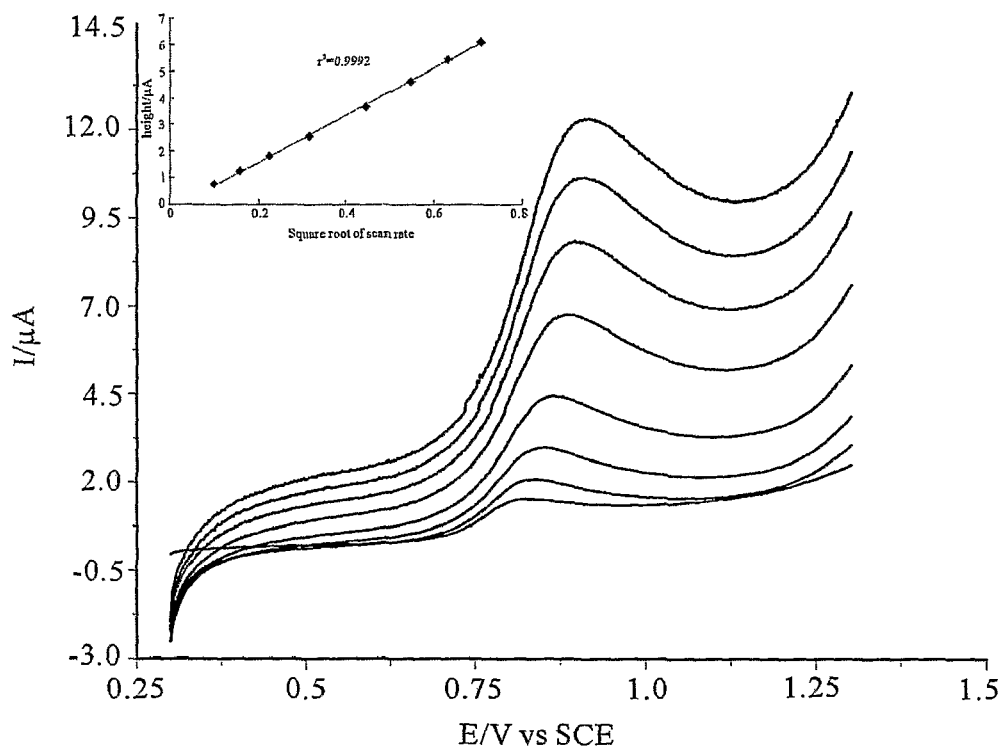
FIG. 4 shows direct anodic scan voltammograms of 100 µm As (III) in 0.1 M $H_2SO_4$ at the electrode described in the context of FIG. 2a at various scan rates. The insert is a plot of peak height vs square root of scan rate.

Direct Anodic Scan Voltammetry of as (III) on Platinum Nanoparticle-Modified Electrodes Direct anodic scan voltammetry was also used to detect As (III) in the range between +0.3 V and 1.3 V (vs SCE). To avoid the deposition of As (0), the scan potential started at +0.3 V (vs SCE). Various scan rates were compared on a platinum nanoparticle-modified GC electrode in 0.1 M $H_2SO_4$ containing 100 μM As (III). The voltammograms are shown in FIG. 4, the insert of which shows a plot of peak height vs square root of scan rate. The peak heights show a good linear relationship with the square root of the scan rate, indicative of a diffusion-controlled process.

Several supporting electrolytes were compared in respect of the response towards As (III) on the platinum nanoparticle-modified electrodes. The electrolyte solutions included $HClO_4$, $H_2SO_4$, $HNO_3$ and $H_3PO_4$. The concentration of the solutions was 1 M. 0.1 M $H_2SO_4$ was also included in the comparison. For each 1 M solution, the sensitivities of the peak heights vs the concentration of As (III) were nearly the same. The sensitivity of 1 M $H_2SO_4$ was slightly higher than 0.1 M $H_2SO_4$.

Calibration and Limit of Detection

Calibration plots were made using platinum nanoparticle-modified GC electrodes with the optimal deposition conditions with standard additions of As (III) (1 μM each). Calibration experiments were performed using direct anodic scan voltammetry in 1 M $HClO_4$ with a scan rate of 500 mVs$^{-1}$. The calibration slope was 0.22 A/M and the LOD (S/N=3) [Harris D C (2003) Quantitative Chemical Analysis (sixth edition). W. H. Freeman and Company, New York] was calculated to be 0.028±0.003 μM (2.1±0.23 ppb). Using a platinum macroelectrode (geometric area of 0.07 cm$^2$) with the same method, the LOD was 0.48±0.02 μM (35±1.5 ppb). The World Health Organization's guideline value of arsenic in drinking water is 10 ppb; the invention may have utility in this context.

EXAMPLE 2

Preparation of Gold Nanoparticle-Modified ITO Electrodes

Gold nanoparticle-modified ITO electrodes were prepared by direct electrodeposition from 0.5 M $H_2SO_4$ containing 0.1 mM $AuCl_4^-$. The resulting electrode surfaces were characterized by AFM.

A sheet of ITO was sonicated in acetone, ethanol and distilled water for 10 mins. After cleaning, the glass sheet was immersed into the solution of $AuCl_4^-$ in 0.5 M $H_2SO_4$ and a potential step from +1.055 V (vs. SCE) to −0.045 V was applied for a fixed time (15 s, 50 s, 150 s or 300 s). All solutions were de-gassed with a $N_2$ stream prior to each measurement.

Figure 5:
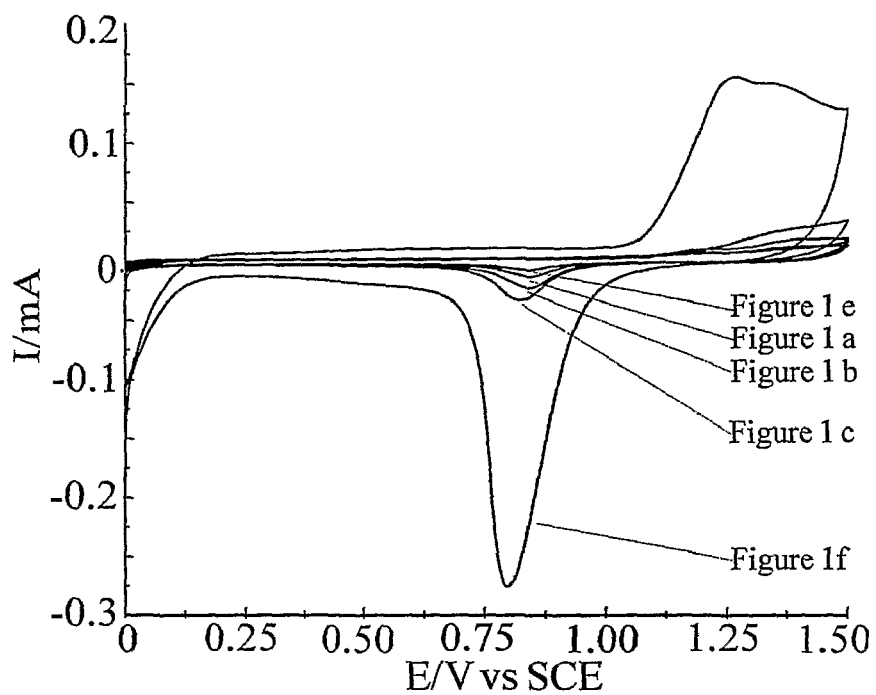
FIG. 5 shows cyclic voltammograms of gold nanoparticle-modified ITO electrodes in 0.05 M $H_2SO_4$. The potential scan rate was 100 mV $s^{-1}$.

In all cases, dispersed gold nanoparticles were found on the substrates. In order to obtain surface information about the electrodeposited gold nanoparticles on ITO film coated glass electrodes, cyclic voltammetric profiles of each electrode under various formation conditions were recorded in 0.05 M $H_2SO_4$ in the potential range from 0 V to 1.5 V (vs. SCE) with the scan rate of 100 mV s$^{-1}$ (FIG. 5). The real surface area of the gold nanoparticle loading on ITO film coated glass electrode was estimated based on the amount of charge consumed during the reduction of the gold surface oxide monolayer and a reported value of 400 µC cm$^{-2}$ (see Kozlowska et al., J. Electroanal. Chem., 1987, 228, 429; and Trasatti et al, Pure Appl. Chem., 1991, 63, 711) was used for the calculation.

The $AuCl_4^-$ concentrations, deposition times, surface areas and sensitivities of the electrodes are summarised in Table 1. It was observed that an increase in the deposition time enhanced the average particle size of the gold nanoparticles. Increasing the concentration of $AuCl_4^-$ solution also caused an increase in particle size. Applying several cycles of short time potential step results in more uniform nanoparticles.

TABLE 1

| FIG. | $AuCl_4^-$ concentration/ mM | Deposition time/s | Total surface area of gold nanoparticles/ cm$^2$ | Sensitivity/ A·cm$^{-2}$·M$^{-1}$ |
| --- | --- | --- | --- | --- |
| 1 a | 0.1 | 50 | 0.04 | 24.3 |
| 1 b | 0.1 | 150 | 0.09 | 19.4 |
| 1 c | 0.1 | 300 | 0.12 | 58.8 |
| 1 d | 0.1 | 20 × 15 s | 0.07 | 60.7 |
| 1 e | 0.01 | 300 | 0.02 | 33.4 |
| 1 f | 1.0 | 300 | 1.08 | 53.2 |

EXAMPLE 3

Detection of Arsenic Using Gold Nanoparticle-Modified ITO Electrodes

Figure 6:
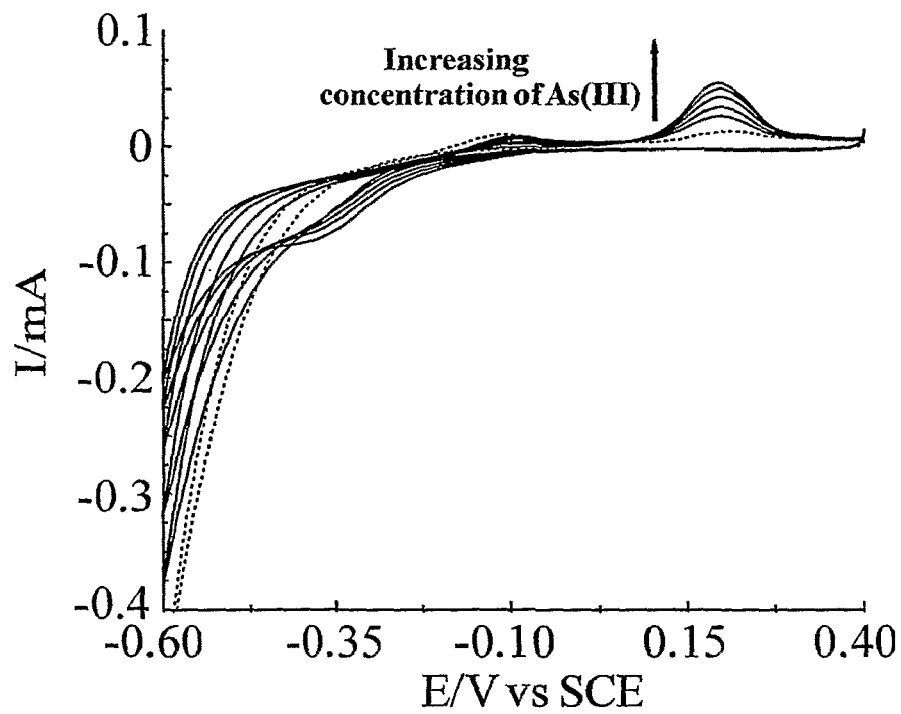
FIG. 6 shows the cyclovoltammetric response of As (III) (1 mM each) at a gold nanoparticle-modified ITO electrode prepared from 0.1 mM $AuCl_4^-$ in 0.5 M $H_2SO_4$ by applying a potential step from +1.055 V to −0.045 V (vs. SCE) for 300 s. The potential scan rate was 100 mV $s^{-1}$.

Cyclic voltammetry was first employed to examine the electroanalytical performance of gold nanoparticle-modified electrodes. FIG. 6 illustrates typical cyclic voltammetric responses in the range from −0.6 V to +0.4 V (vs. SCE, 100 mV s$^{-1}$) at a gold nanoparticle-modified electrode (stepped from 1.055 V to −0.045 V for 300 s from 0.5 M $H_2SO_4$ containing 0.1 mM $AuCl_4$) in 1 M HCl. It can be seen in FIG. 6 that no redox processes were registered in the potential range studied in the blank solution (dashed line). A new reduction wave emerged at −0.35 V (vs. SCE) upon the addition of 1 µM As (III) and is attributable to the three electron reduction of As (III) to As (0). On the reversal anodic scan, an oxidation wave at +0.25 V (vs. SCE) was observed. This process is attributable to the subsequent re-oxidation of As (0) to the parent As (III) species. Both waves were found to increase linearly with further additions of As (III).

Figure 7:
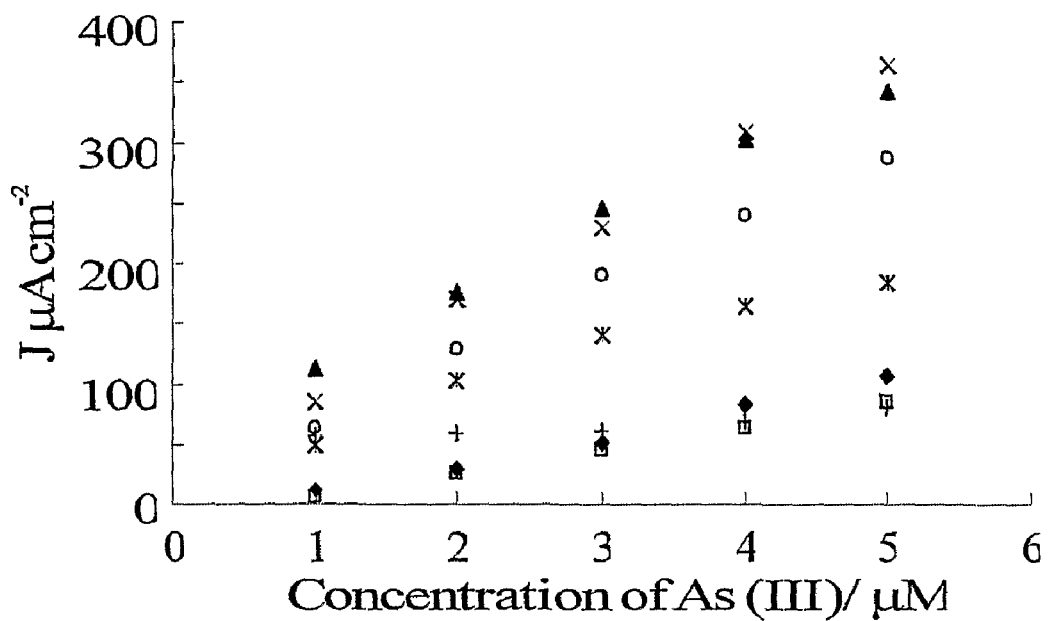
FIG. 7 shows plots of current densities vs. concentration of As (III) at various gold nanoparticle-modified ITO electrodes and a gold macroelectrode. The preparation conditions of the ITO electrodes were ($AuCl_4$ concentration/deposition time): (♦) 0.1 mM/50 s, (○) 0.1 mM 1150 s, (X) 0.1 mM/300 s, (▲) 0.1 mM/20 times 15 s, (*) 0.01 mM/300 s, (□) 1.0 mM/300 s. The gold macroelectrode is represented by (+).

Plots of current densities vs. concentration of As (III) at different gold nanoparticle-modified ITO electrodes and a gold macroelectrode are shown in FIG. 7. The sensitivities are summarised in Table 1 supra. It was observed that increasing the deposition time led to an increase in sensitivity. The sensitivities of the gold nanoparticle-modified electrodes were greater than that of the gold macroelectrode (5.9 A·cm$^{-2}$·M$^{-1}$).

Modified electrodes prepared using 0.1 mM $AuCl_4^-$ with a deposition time of 300 s had the highest sensitivity, and were used in the following experiments.

Figure 8:
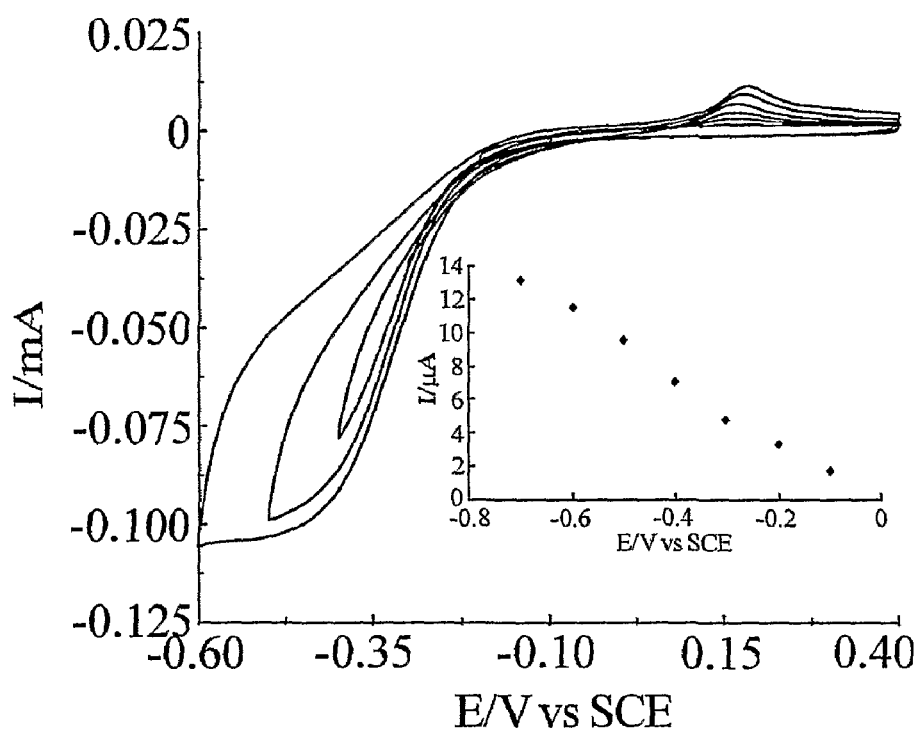
FIG. 8 shows cyclic voltammograms of 10 µM As (III) in 1 M HCl at different reverse potential at a gold nanoparticle-modified ITO electrode prepared from 0.1 mM $AuCl_4$ in 0.5 M $H_2SO_4$ by applying potential step from +1.055 V to −0.045 V (vs. SCE) for 300 s. The potential scan rate was 100 mV $s^{-1}$. The insert shows plots of peak currents vs. reverse potential.

Different reverse potentials were examined with cyclic voltammetry in 1 M HCl containing 10 µM As (III). The resulting voltammograms are shown in FIG. 8. The start potential was kept at +0.4 V (vs. SCE), while the reverse potential was −0.1 V, −0.2 V, −0.3 V, −0.4 V, −0.5 V, −0.6 V (vs. SCE), respectively. It was observed that a more negative potential can be used on the electrodes of the invention, compared with gold macroelectrodes.

Linear sweep voltammetry was next employed for the determination of As (III). The deposition potential was −0.6 V with 60 s deposition time. 1 M HCl, $H_2SO_4$ and $HNO_3$ were compared as the supporting electrolytes. In 1 M HCl and $H_2SO_4$, another peak appeared at ca. +0.1 V, which is attributable to oxygen. In 1 M $HNO_3$, the effect of oxygen was minimised. Longer deposition times (120 s, 180 s and 300 s) were also used, but the deposition of oxygen increased significantly with the increase of deposition time.

The limit of detection (S/N=3; Harris, Quantitative Chemical Analysis (sixth edition), W. H. Freeman and Company, New York, 2003) was calculated to be 5±0.2 ppb with deposition at −0.6 V for 60 sec in 1 M $HNO_3$. The World Health Organization's guideline value of arsenic in drinking water is 10 ppb; the invention may therefore have utility in this context.

The invention claimed is:

1. A method of detecting arsenic in a sample, which comprises the steps of contacting the sample with working and counter electrodes in the presence of an electrolyte, and determining the electrochemical response of the working electrode to the sample, wherein the working electrode comprises particulate platinum, and wherein the sample comprises one or more metals selected from copper, lead, zinc, iron, antimony, silver, selenium, bismuth and mercury.

2. A method according to claim 1, which comprises applying a potential across the electrodes and determining the electrochemical response of the working electrode to the sample.

3. A method according to claim 2, wherein the potential is applied relative to a reference electrode, for example a saturated calomel electrode.

4. A method according to claim 3, wherein the applied potential is varied relative to the reference electrode and the voltammetric response determined.

5. A method according to claim 1, wherein the sample comprises copper.

6. A method according to claim 1, wherein the sample is a liquid.

7. A method according to claim 6, wherein the sample is an aqueous sample.

8. A method according to claim 1, wherein the electrolyte is present in solution.

9. A method according to claim 1, wherein the electrolyte comprises $HClO_4$, $H_2SO_4$, $HNO_3$ or $H_3PO_4$.

10. A method according to claim 1, wherein the working electrode comprises glassy carbon.

11. A method according to claim 1, wherein the working electrode comprises nanoparticulate platinum.

12. A method according to claim 1, wherein the diameter of the or each particle is from about 25 to about 200 nm, for example from about 50 to about 175 nm.

13. A method according to claim 1, wherein the counter electrode comprises platinum.

* * * * *